United States Patent [19]

Kübbeler et al.

[11] 4,333,884
[45] Jun. 8, 1982

[54] PRODUCTION OF ACETIC ANHYDRIDE

[75] Inventors: Hans-Klaus Kübbeler, Swisttal; Heinz Erpenbach, Cologne; Klaus Gehrmann; Klaus Schmitz, both of Erftstadt, all of Fed. Rep. of Germany

[73] Assignee: Hoechst Aktiengesellschaft, Fed. Rep. of Germany

[21] Appl. No.: 191,702

[22] Filed: Sep. 29, 1980

[30] Foreign Application Priority Data

Oct. 2, 1979 [DE] Fed. Rep. of Germany ....... 2939839

[51] Int. Cl.³ ..................... C07C 51/56; C07C 51/54; C07C 53/12
[52] U.S. Cl. ................................... 260/546; 260/549
[58] Field of Search ............................. 260/546, 549

[56] References Cited
U.S. PATENT DOCUMENTS
4,115,444 9/1978 Rizkalla .

FOREIGN PATENT DOCUMENTS 8396 3/1980 European Pat. Off. ........... 260/549

*Primary Examiner*—Natalie Trousof
*Assistant Examiner*—Frederick W. Pepper
*Attorney, Agent, or Firm*—Connolly and Hutz

[57] ABSTRACT

The invention relates to an improved process for making acetic anhydride by reacting methyl acetate and/or dimethylether with carbon monoxide under practically anhydrous conditions, at temperatures of 350 to 575 K., under pressures of 1 to 300 bars, and in the presence of a catalyst system containing noble metals belonging to group VIII of the periodic system of the elements, or compounds thereof, iodine and/or its compounds, and an aliphatic carboxylic acid having 1 to 8 carbon atoms. The improved process is effected in the presence of a catalyst system containing, as additional ingredients, a heterocyclic aromatic compound, in which at least one hetero atom is a quaternary nitrogen atom, or a quaternary organophosphorus compound, and a zirconium compound being soluble in the reaction mixture.

7 Claims, 1 Drawing Figure

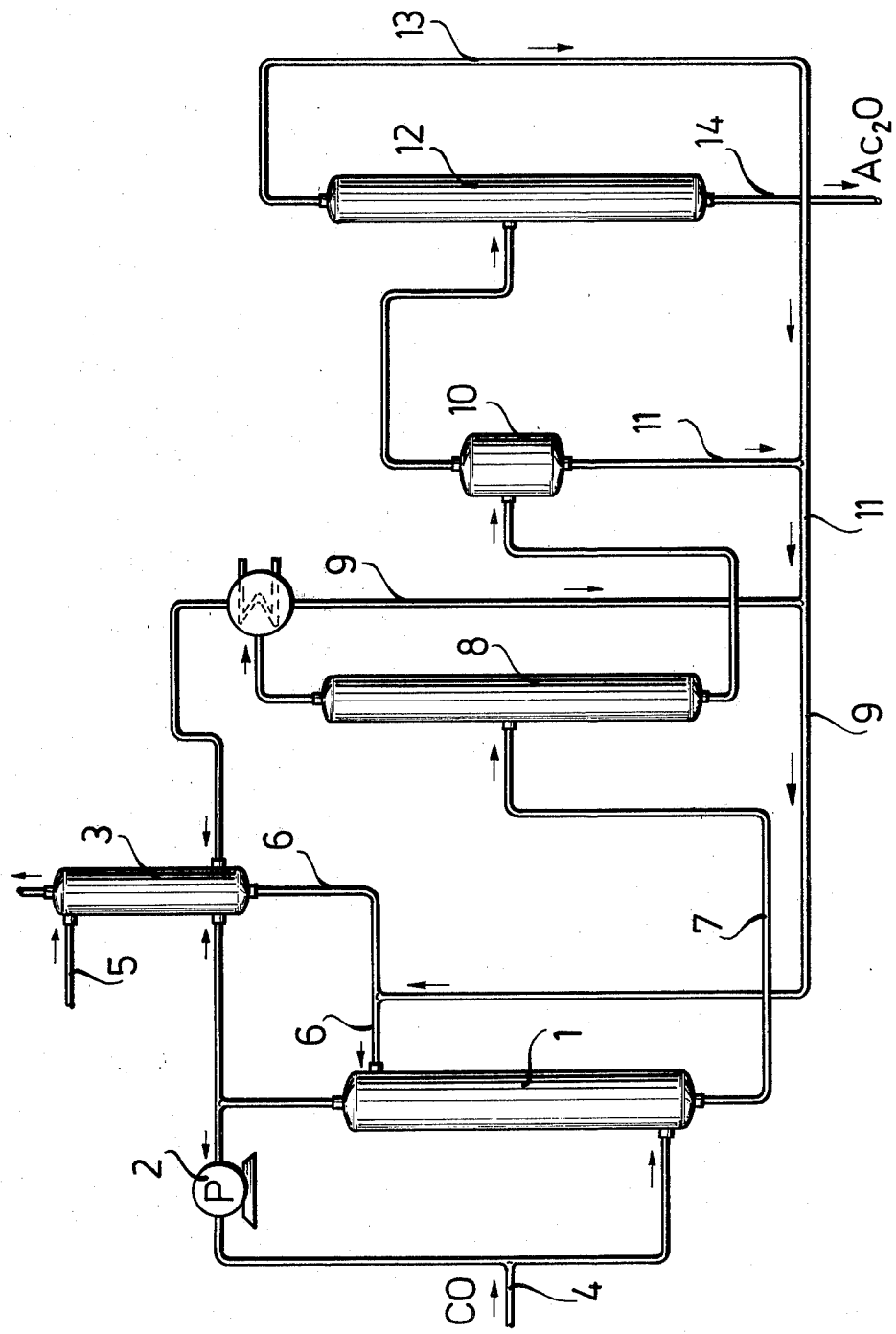

PRODUCTION OF ACETIC ANHYDRIDE

The present invention relates to a process for making acetic anhydride by reacting methyl acetate and/or dimethylether with carbon monoxide under practically anhydrous conditions, at temperatures of 350 to 575 K., under pressures of 1 to 300 bars, and in the presence of a catalyst system containing noble metals belonging to group VIII of the periodic system of the elements, or compounds thereof, iodine and/or its compounds, and an aliphatic carboxylic acid having 1 to 8 carbon atoms, the process comprising: effecting the reaction in the presence of a catalyst system containing, an additional ingredients, a heterocyclic aromatic compound, in which at least one hetero atom is a quaternary nitrogen atom, or a quaternary organophosphorus compound, and a zirconium compound being soluble in the reaction mixture.

A comparable process for making monocarboxylic anhydrides has been described in German patent specification "Offenlegungsschrift" No. 2 610 036, wherein, however, the noble metal belonging to group VIII of the periodic system of the elements and iodide are used in combination with a multiple promoter containing a metal, preferably chromium, as well as an organonitrogen or organophosphorus compound with trivalent nitrogen or phosphorus therein.

The process disclosed in German patent specification "Offenlegungsschrift" No. 2 610 036 is seriously handicapped by the fact that the metal compounds and secondary products of the multiple promoter are substantially insoluble in boiling acetic anhydride, so that the circulation of the catalyst/promoter-system, which is necessary for continuous operation, is rendered very difficult or even impossible. In addition to this, the above insoluble compounds have been found unduly to affect the separation of acetic anhydride from the catalyst-system. During distillative work-up of the reaction mixture, for example, the evaporator is liable to become covered with green chromium salts which significantly impair the desirable transfer of heat. This makes it naturally necessary for the evaporator temperature to be increased which has considerable adverse effects on the catalyst system. As a result, it is necessary for the expensive noble metal-containing catalyst to be subjected to cumbersome intermediate processing treatment with undesirable loss of valuable catalyst and rapid adverse effects on the activity of the entire system. These are the reasons why the process just described has not been commercialized heretofore.

Attempts to avoid these adverse effects have already been made and described in German Patent Application No. P 28 36 084.1 which has not yet been published. In the process disclosed therein, the system comprised of chromium compounds and organonitrogen or organophosphorus compounds containing trivalent nitrogen or phosphorus is replaced by a heterocyclic aromatic compound containing quaternary nitrogen in combination with an aliphatic carboxylic acid. Under the reaction conditions of this process, the addition compounds with quaternary nitrogen are in the form of a melt and do in no way interfere with the circulation of the catalyst system. Nor do the substitute products impair the selectivity of the catalyst system of which the activity is even improved considerably. Both under the reaction conditions and the conditions selected for the work-up of the products obtained by the carbonylation of methyl acetate and dimethylether, the heterocyclic aromatic compounds with at least one quaternary nitrogen as the hetero atom, which are used individually or in combination, are in the form of a melt which is a suitable solvent for the noble metal complexes and is also readily miscible with acetic anhydride.

The process of this invention has unexpectedly been found significantly to increase the catalyst activity, expressed in grams acetic anhydride obtained per gram elementary noble metal per hour.

This is more especially an unexpected result inasmuch as zirconium compounds or individual representatives thereof would not have been expected to be soluble in the reaction system in the absence of any indication in the prior literature that zirconium compounds indeed play a particular part in the carbonylation of esters and/or ethers.

Zirconium compounds useful in the process of this invention comprise, e.g. zirconium halide, zirconyl halide, zirconium acetate, zirconyl acetate, organozirconium compounds, such as bis(cyclopentadienyl) zirconium dihalide. Useful halides are the chlorides, bromides and iodides.

Further preferred features of the present invention provide:
(a) for the heterocyclic compounds or organophosphorus compounds used to have a melting point or mixed melting point of less than 413 K., which is the boiling point of acetic anhydride;
(b) for the heterocyclic compounds or organophosphorus compounds to be used in the form of their addition products with acetic acid or methyl iodide;
(c) for the catalyst system comprised of noble metal (compound)/zirconium compound/iodine(compound)/carboxylic acid/heterocyclic compound or organophosphorus compound to be used in an atomic or molar ratio of 1:(0.1–10):(1–1400):(10–2000):(1–1200); and
(d) for a carbon monoxide/hydrogen mixture containing up to 20 volume% hydrogen to be used.

Useful heterocyclic aromatic compounds and useful quaternary organophosphorus compounds which form melts, under the reaction conditions and also under the conditions selected for the work-up of the products obtained by the carbonylation of methyl acetate or dimethylether, and are suitable solvents for the noble metal complexes and zirconium compounds, and are readily miscible with acetic anhydride, comprise, for example:
(1) N-methylpyridinium iodide; N,N-dimethylimidazolium iodide; N-methyl-3-picolinium iodide; N-methyl-2,4-lutidinium iodide; N-methyl-3,4-lutidinium iodide; N-methyl-quinolinium iodide;
(2) tributyl-methyl-phosphonium iodide; trioctyl-methyl-phosphonium iodide; trilauryl-methyl-phosphonium iodide; triphenyl-methyl-phosphonium iodide; and
(3) pyridinium acetate; N-methylimidazolium acetate; 3-picolinium acetate; 2,4-lutidinium acetate; 3,4-lutidinium acetate.

Sometimes, it may be preferable for the present process to be effected in the presence of a catalyst system containing several heterocyclic aromatic compounds or several quaternary organophosphorus compounds.

The promoter properties of these addition products are considerably improved in the presence of an aliphatic carboxylic acid with 1 to 18 carbon atoms.

The process of the present invention should preferably be effected at temperatures of 400 to 475 K. and under pressures of 20 to 150 bars. It is also preferable to use 0.0001 to 0.01 mol of the noble metal belonging to group VIII of the periodic system of the elements or its compounds per mol of methyl acetate and/or dimethylether. Further preferred features provide for the catalyst system of noble metal (compound)/zirconium compound/iodine (compound)/carboxylic acid/heterocyclic compound or organophosphorus compound to be used in an atomic or molar ratio of 1:(0.5–8):(10–300):(25–600):(10–300), and for acetic acid to be used as the carboxylic acid.

The invention will now be described with reference to the accompanying diagrammatic representation showing a typical form of flow scheme for carrying out the present process.

Methyl acetate and/or dimethylether and carbon monoxide or a mixture of CO and $H_2$ containing up to 20 volume% of $H_2$ are placed in an autoclave 1 made up of Hastelloy C and reacted therein under a preferred pressure of 20 to 150 bars and at a preferred temperature of 400 to 475 K. to give acetic anhydride, the reaction being effected in the presence of a catalyst system comprised of one or more noble metals belonging to group VIII of the periodic system or their compounds and iodine and/or its compounds, preferably methyl iodide, with addition of one or more zirconium compounds soluble in the reaction mixture, and in the presence of a carboxylic acid, preferably acetic acid, and at least one heterocyclic aromatic compound, in which at least one hetero atom is a quaternary nitrogen atom, or a quaternary organophosphorus compound. The bulk of unreacted carbon monoxide and hydrogen, if any, is circulated by means of a gas recirculation pump 2, whilst a fraction thereof is allowed to issue from the system via a scrubbing stage 3. Fresh carbon monoxide, which may be used in admixture with hydrogen, is introduced into the gas under circulation via a conduit 4 in metered proportions corresponding to the conversion rate. Fresh methyl acetate and/or dimethylether are supplied in quantities corresponding to the conversion rate via a conduit 5 opening into the upper portion of the scrubbing stage 3 and introduced into the reactor 1 through a conduit 6. The reaction mixture issues from the reactor 1 through a conduit 7. The distilling column 8 is used to effect the separation of the low-boiling fractions (methyl-acetate or dimethylether, methyl iodide) which are recycled to the reactor 1 via conduits 9 and 6. Material accumulating in the base portion of column 8 is delivered to an evaporator 10 and separated into distillate and catalyst. This latter is recycled through conduits 11, 9 and 6 into the reactor 1. The distillate recovered in the evaporator 10 is separated in distilling column 12 into acetic acid, which is recycled to the reactor 1 through conduits 13, 11, 9 and 6, and acetic anhydride, which is removed through conduit 14.

EXAMPLE 1

250 g methyl acetate, 1.6 g $RhCl_3.3H_2O$, 5 g $ZrCl_4$, 60 g $CH_3I$, 70 g acetic acid and 70 g N,N-dimethylimidazolium iodide were placed in a Hastelloy autoclave and reacted therein with CO at 455 K. under 50 bars. After a reaction period of 15 minutes, the reaction mixture was found to contain 281 g acetic anhydride, corresponding to 1797 g $Ac_2O$ per g Rh per hour.

EXAMPLE 1a (Comparative Example = Example 5 of German Patent Application P 28 36 084.1)

250 g methyl acetate, 1.6 g $RhCl_3.3H_2O$, 60 g $CH_3I$, 70 g acetic acid and 70 g N,N-dimethylimidazolium iodide were placed in a Hastelloy autoclave and reacted therein with CO at 450 K. under 50 bars. After a reaction period of 31 minutes, the reaction mixture was found to contain 283 g acetic anhydride, corresponding to 876 g $Ac_2O$ per g Rh per hour.

EXAMPLE 2

200 g dimethylether, 1.8 g $RhCl_3.3H_2O$, 5 g $ZrCl_4$, 70 g $CH_3I$, 100 g acetic acid and 80 g N-methyl-3-picolinium iodide were placed in a Hastelloy autoclave and reacted therein with CO at 455 K. under 60 bars. After a reaction period of 12 minutes, the reaction mixture was found to contain 312 g acetic anhydride, corresponding to 2217 g $Ac_2O$ per g Rh per hour.

The reaction product containing methyl acetate contained less than 0.1 mass% dimethylether.

EXAMPLE 3

280 g methyl acetate, 1.8 g $RhCl_3.3H_2O$, 8 g $ZrOCl_2.8H_2O$, 90 g $CH_3I$, 70 g acetic acid and 70 g N,N-dimethylimidazolium iodide were placed in a zirconium-lined autoclave and reacted therein with CO at 450 K. under 50 bars. After a reaction period of 14 minutes, 286 g acetic anhydride, corresponding to 1742 g $Ac_2O$ per g Rh per hour, was found to have been formed.

EXAMPLE 4 (Outside invention)

250 g methyl acetate, 1.6 g $RhCl_3.3H_2O$, 3 g $ZrO_2$, 60 g $CH_3I$, 60 g acetic acid and 80 g N-methyl-3-picolinium iodide were placed in a Hastelloy autoclave and reacted therein with CO at 450 K. under 60 bars. After a reaction period of 32 minutes, 281 g acetic anhydride, corresponding to 843 g $Ac_2O$ per g Rh per hour, was found to have been formed. As can be inferred from the catalyst efficiency, the addition of $ZrO_2$ which is insoluble in the reaction medium, could not be found to influence the activity of the catalyst system (cf. comparative Example 1a).

EXAMPLE 5

280 g methyl acetate, 1.8 g $IrCl_3$, 8 g $ZrOCl_2.8H_2O$, 60 g $CH_3I$, 50 g acetic acid and 100 g N-methylquinolinium iodide were placed in a Hastelloy autoclave and reacted therein with CO at 465 K. under 80 bars. After 38 minutes, analysis indicated the formation of 273 g acetic anhydride, corresponding to 372 g $Ac_2O$ per g Ir per hour.

EXAMPLE 6

260 g methyl acetate, 1.6 g $RhCl_3.3H_2O$, 8 g $ZrOCl_2.8H_2O$, 70 g $CH_3I$, 60 g acetic acid and 60 g N,N-dimethylimidazolium iodide were placed in a Hastelloy autoclave and reacted therein at 445 K. under 60 bars with a mixture of CO and $H_2$, which contained 8 volume% $H_2$. After 18 minutes, the reaction mixture was found to contain 281 g acetic anhydride, corresponding to 1498 g $Ac_2O$ per g Rh per hour. The reaction mixture contained less than 0.1 mass% ethylidene diacetate.

EXAMPLE 7

280 g methyl acetate, 2 g Pd(OAc)$_2$, 10 g ZrOI$_2$.8-H$_2$O, 70 g acetic acid, 20 g N-methylpyridinium iodide and 40 g N-methyl-3-picolinium iodide were placed in a Hastelloy autoclave and reacted therein with CO at 460 K. under 50 bars. After 78 minutes, 197 g acetic anhydride, corresponding to 160 g Ac$_2$O per g Pd per hour, was obtained.

EXAMPLE 8

260 g methyl acetate, 1.6 g RhCl$_3$.3H$_2$O, 2 g ZrOCl$_2$.8H$_2$O, 70 g CH$_3$I, 70 g acetic acid and 60 g N,N-dimethylimidazolium iodide were placed in a Hastelloy autoclave and reacted therein with CO at 445 K. under 60 bars. After 24 minutes, 278 g acetic anhydride, corresponding to 1110 g Ac$_2$O per g Rh per hour, was obtained.

EXAMPLE 9

250 g methyl acetate, 1.6 g RhCl$_3$.3H$_2$O, 7 g bis(cyclopentadienyl)zirconium dichloride, 70 g CH$_3$I, 60 g acetic acid and 60 g N,N-dimethylimidazolium iodide were placed in a Hastelloy autoclave and reacted therein with CO at 450 K. under 60 bars. After 14 minutes, 292 g acetic anhydride, corresponding to 1999 g Ac$_2$O per g Rh per hour, was obtained.

EXAMPLE 10

250 g methyl acetate, 1.6 g RhCl$_3$.3H$_2$O, 10 g ZrOCl$_2$.H$_2$O, 150 g CH$_3$I, 75 g acetic acid and 100 g N-methylimidazolium acetate were placed in a zirconium-lined autoclave and reacted therein with CO at 445 K. under 60 bars. After 19 minutes, the reaction mixture was found to contain 284 g acetic anhydride, corresponding to 1433 g Ac$_2$O per g Rh per hour.

EXAMPLE 11

250 g methyl acetate, 0.8 g RhCl$_3$.3H$_2$O, 5 g ZrCl$_4$, 90 g CH$_3$I, 90 g acetic acid, 120 g N,N-dimethylimidazolium iodide and 60 g N-methyl-3-picolinium iodide were placed in a Hastelloy autoclave and reacted therein with CO at 445 K. under 70 bars. After a reaction period of 24 minutes, 283 g acetic anhydride, corresponding to 2263 g Ac$_2$O per g Rh per hour, was obtained.

EXAMPLE 12

280 g methyl acetate, 2.7 g Pd(OAc)$_2$, 10 g ZrOCl$_2$.8H$_2$O, 60 g CH$_3$I, 60 g acetic acid and 200 g trilauryl methyl-phosphonium iodide were placed in a Hastelloy autoclave and reacted therein at 450 K. under 80 bars with a mixture of CO and H$_2$ which contained 15 volume% H$_2$. After 19 minutes, the reaction mixture was found to contain 278 g acetic anhydride, corresponding to 686 g Ac$_2$O per g Pd per hour.

EXAMPLE 13

250 g methyl acetate, 2.7 g Pd(OAc)$_2$, 6 g ZrCl$_4$, 70 g CH$_3$I, 70 g acetic acid and 150 g tributyl-methyl-phosphonium iodide were placed in a Hastelloy autoclave and reacted therein at 460 K. under 100 bars with a mixture of CO and H$_2$ which contained 10 volume% H$_2$. After 15 minutes, the reaction mixture was found to contain 273 g acetic anhydride, corresponding to 853 g Ac$_2$O per g Pd per hour.

EXAMPLE 14

280 g methyl acetate, 0.8 g RhCl$_3$.3H$_2$O, 8 g ZrOCl$_2$.8H$_2$O, 60 g CH$_3$I, 70 g acetic acid and 150 g trioctyl-methyl-phosphonium iodide were placed in a Hastelloy autoclave and reacted therein with CO at 450 K. under 60 bars. After 35 minutes, the reaction mixture was found to contain 281 g acetic anhydride, corresponding to an efficiency of 1540 g Ac$_2$O per g Rh per hour.

EXAMPLE 15

280 g methyl acetate, 2.7 g Pd(OAc)$_2$, 8 g ZrCl$_4$, 60 g CH$_3$I, 70 g acetic acid, 70 g tributyl-methyl-phosphonium iodide and 70 g methyltriphenyl-phosphonium iodide were placed in a Hastelloy autoclave and reacted therein at 460 K. under 100 bars with a mixture of CO and H$_2$ which contained 9 volume% H$_2$. After 17 minutes, the reaction mixture was found to contain 299 g acetic anhydride, corresponding to an efficiency of 824 g Ac$_2$O per g Pd per hour.

We claim:

1. In a process for making acetic anhydride by reacting methyl acetate and/or dimethylether with carbon monoxide under practically anhydrous conditions, at temperatures of 350 to 575 K., under pressures of 1 to 300 bars, and in the presence of a catalyst system containing noble metals belonging to group VIII of the periodic system of the elements, or compounds thereof, iodine and/or its compounds, and an aliphatic carboxylic acid having 1 to 8 carbon atoms, the improvement which comprises: effecting the reaction in the presence of a catalyst system containing, as additional ingredients, a heterocyclic aromatic compound, in which at least one hetero atom is a quaternary nitrogen atom, or a quaternary organophosphorus compound, and a zirconium compound being soluble in the reaction mixture; said heterocyclic compound or organophosphorus compound being in the form of its addition product with acetic acid or methyl iodide and having a melting point or mixed melting point of less than 413 K., which is the boiling point of acetic anhydride.

2. A process as claimed in claim 1, wherein the catalyst system comprised of noble metal (compound)/zirconium compound/iodine(compound)/carboxylic acid/heterocyclic compound or organophosphorus compound is used in an atomic or molar ratio of 1:(0.1–10):(1–1400):(10–2000):(1:1200).

3. A process as claimed in claim 1, wherein a carbon monoxide/hydrogen-mixture containing up to 20 volume% of hydrogen is used.

4. In a process for making acetic anhydride by reacting methyl acetate and/or dimethylether with carbon monoxide under practically anhydrous conditions, at temperatures of 350 to 575 K., under pressures of 1 to 300 bars, and in the presence of a catalyst system containing noble metals belonging to Group VIII of the periodic system of the elements, or compounds thereof, iodine and/or its compounds, and an aliphatic carboxylic acid having 1 to 8 carbon atoms, the improvement which comprises: effecting the reaction in the presence of a catalyst system containing, as additional ingredients, a heterocyclic aromatic compound selected from the group consisting of N-methyl-pyridinium iodide; N-N-dimethylimidazoliumiodide; N-methyl-3-picolinium iodide; N-methyl-2,4-lutidinium iodide; N-methyl-3,4-lutidinium iodide; N-methyl-quinolinium iodide; pyridinium acetate; N-methylimidazolium acetate; 3-picolinium acetate; 2,4-lutidinium acetate or 3,4-lutidinium acetate, or a quaternary organophosphorus compound selected from the group consisting of tributylmethyl-phosphonium iodide; trioctylmethyl-phosphonium iodide; trilauryl-methyl-phosphonium iodide or triphenyl-methyl-phosphonium iodide; and a zirconium compound being soluble in the reaction mixture.

5. A process as claimed in claim 4 wherein the catalyst system comprised of noble metal (compound)/zirconium compound/iodine (compound)/carboxylic acid/heterocyclic compound or organophosphorus compound is used in an atomic or molar ratio of 1:(0.1–10):(1–1400):(10–2000):(1:1200).

6. A process as claimed in claim 4, wherein a carbonmonoxide/hydrogen mixture containing up to 20 volume % of hydrogen is used.

7. The process of claim 4, wherein the iodine and/or its compounds is selected from the group consisting of iodine and methyliodide.

* * * * *